(12) United States Patent
Wirth et al.

(10) Patent No.: US 8,703,991 B2
(45) Date of Patent: Apr. 22, 2014

(54) SYNTHESIS OF (PHENYLALKYLOXY)PHENYL-OXOBUTANOIC ACIDS

(75) Inventors: David D. Wirth, Oak Ridge, NC (US); James P. Hudspeth, San Diego, CA (US); Richard Hudspeth, legal representative, San Diego, CA (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 235 days.

(21) Appl. No.: 13/127,120

(22) PCT Filed: Nov. 3, 2009

(86) PCT No.: PCT/US2009/063096
§ 371 (c)(1),
(2), (4) Date: Jun. 21, 2011

(87) PCT Pub. No.: WO2010/053910
PCT Pub. Date: May 14, 2010

(65) Prior Publication Data
US 2012/0004442 A1    Jan. 5, 2012

Related U.S. Application Data

(60) Provisional application No. 61/111,133, filed on Nov. 4, 2008.

(51) Int. Cl.
*C07C 69/38*    (2006.01)

(52) U.S. Cl.
USPC ............................ 560/82; 560/23; 560/53

(58) Field of Classification Search
USPC ................... 568/43; 560/53, 23, 82
See application file for complete search history.

(56) References Cited

U.S. PATENT DOCUMENTS

| | | | |
|---|---|---|---|
| 3,932,498 A * | 1/1976 | Shen et al. | 562/428 |
| 4,013,692 A | 3/1977 | Scherrer | |
| 4,265,903 A | 5/1981 | Cohnen | |
| 4,492,799 A * | 1/1985 | Wheeler | 562/506 |
| 4,626,543 A | 12/1986 | Kollmeyer | |
| 5,284,971 A | 2/1994 | Walker et al. | |
| 6,166,053 A * | 12/2000 | Sperl et al. | 514/357 |
| 6,858,602 B2 | 2/2005 | Sharma et al. | |
| 6,916,848 B2 | 7/2005 | Sharma | |
| 6,924,314 B2 | 8/2005 | Sharma et al. | |
| 6,946,491 B2 * | 9/2005 | Sharma et al. | 514/649 |
| 7,012,071 B2 | 3/2006 | Sharma et al. | |
| 7,041,659 B2 | 5/2006 | Sharma | |
| 7,045,541 B2 | 5/2006 | Sharma | |
| 7,101,910 B2 | 9/2006 | Sharma et al. | |
| 7,329,782 B2 | 2/2008 | Sharma | |
| 7,361,686 B2 | 4/2008 | Hodge et al. | |
| 7,442,796 B2 | 10/2008 | Sharma et al. | |
| 7,514,555 B2 | 4/2009 | Hodge et al. | |
| 7,547,802 B2 | 6/2009 | Sharma | |
| 2006/0178537 A1 | 8/2006 | Altmayer et al. | |

FOREIGN PATENT DOCUMENTS

| | | |
|---|---|---|
| WO | 02100341 A2 | 12/2002 |
| WO | 2009137381 A1 | 11/2009 |

OTHER PUBLICATIONS

Web Site; http://courses.chem.psu.edu/chem36/Chem36H/IndivExpt1/805%20Malonic%20Ester%20Synthesis.pdf; Sep. 4, 2006.*

Cowper et al; Web site; http://www.orgsyn.org/orgsyn/orgsyn/prepContent.asp?prep=cv2p0480 (Nov. 4, 2004).*

Pending (as of Jan. 11, 2011) claims from U.S. Appl. No. 12/990,851.

* cited by examiner

*Primary Examiner* — Johann R Richter
*Assistant Examiner* — Pancham Bakshi
(74) *Attorney, Agent, or Firm* — Lewis J. Kreisler

(57) ABSTRACT

A method for synthesizing (phenylalkyloxy)phenyl-oxobutanoic acid compounds is described. The corresponding (phenylalkyloxy)acylphenyl compound is halogenated, giving the alpha haloketone. The halide is displaced by the anion of a di-alkyl malonate to give a substituted malonic ester. Hydrolysis of the ester and decarboxylation of the diacid gives the desired product.

14 Claims, No Drawings

SYNTHESIS OF (PHENYLALKYLOXY)PHENYL-OXOBUTANOIC ACIDS

BACKGROUND OF THE INVENTION

A synthesis of certain (phenylalkyloxy)phenyl-oxobutanoic acid compounds, including 4-[3-(2,6-dimethylbenzyloxy)phenyl]-4-oxobutanoic acid and its ethyl ester, is described in WO 02/100341 A2 (Wellstat Therapeutics Corp.). A different synthesis of 4-[3-(2,6-dimethylbenzyloxy)phenyl]-4-oxobutanoic acid is described in U.S. Patent Application No. 61/050,442 and No. 61/057,410. There is a need for an improved synthesis that does not require low temperatures, uses inexpensive starting materials and gives a good yield.

SUMMARY OF THE INVENTION

This invention provides a method for synthesizing (phenylalkyloxy)phenyl-oxobutanoic acid compounds. The corresponding (phenylalkyloxy)acylphenyl precursor is halogenated, giving the alpha haloketone. The halide is displaced by the anion of diethyl malonate to give a substituted malonic ester. Hydrolysis of the ester and decarboxylation of the diacid gives the desired product.

DETAILED DESCRIPTION OF THE INVENTION

As used herein the abbreviation "DPE" means 3-(2,6-dimethylbenzyloxy)acetophenone. As used herein the abbreviation "DPA" means 4-[3-(2,6-dimethylbenzyloxy)phenyl]-4-oxobutanoic acid. As used herein the abbreviation "NBS" means N-bromosuccinimide. As used herein the abbreviation "NCS" means N-chlorosuccinimide. As used herein "THF" means tetrahydrofuran. As used herein "DMF" means dimethyl formamide. As used herein "DMSO" means dimethyl sulfoxide. As used herein "NMP" means N-Methyl-2-pyrrolidone.

As used herein the transitional term "comprising" is open-ended. A claim utilizing this term can contain elements in addition to those recited in such claim.

This invention provides a method for producing a compound of Formula I

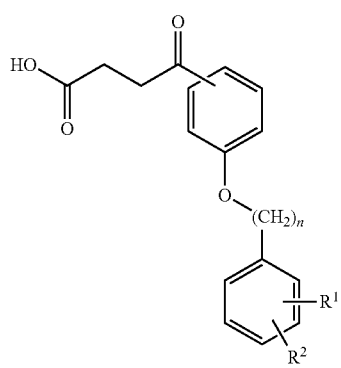

wherein n is 1, 2 or 3; $R^1$ and $R^2$ are each independently selected from the group consisting of halo, alkyl having one or two carbon atoms, perfluoromethyl, alkoxy having one or two carbon atoms, perfluoromethoxy, and hydroxy; comprising:

(a) reacting the corresponding compound of Formula II with a halogenating agent in an ethereal solvent to yield crude compound of Formula III, wherein X is fluoro, chloro, bromo or iodo;

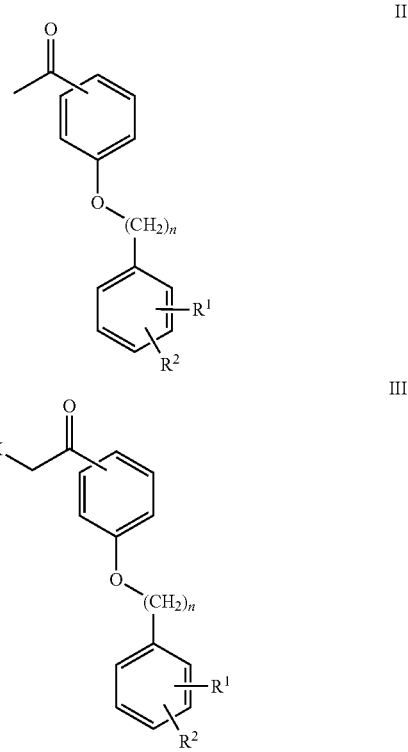

In an embodiment of this invention, in step (a) the halogenating agent is a brominating agent and X is bromo, or the halogenating agent is a chlorinating agent and X is chloro. In more specific embodiments, the brominating agent is bromine and the chlorinating agent is sulfuryl chloride. The reaction of step (a) can be performed at any temperature that is conventional for halogenations reactions. A temperature of from −30° C. to +20° C., for example a temperature of about 0° C. is convenient. In accordance with this invention any ethereal solvent or mixture of ethereal solvents can be utilized in step (a). Examples of acceptable ethereal solvents include diethyl ether, dioxane, tetrahydrofuran (THF), and di-n-butyl ether. The preferred solvent is a mixture of dioxane and di-n-butyl ether.

(a') Optionally triturating the crude compound of Formula III from step (a) to yield solid compound of Formula III;

(b) reacting the compound of Formula III from the previous step (a or a') with a malonate ester represented by the formula $R^3OC(O)CH_2C(O)OR^3$ and a base in a solvent, wherein the solvent comprises an alcohol represented by the formula $R^3OH$, to yield a crude preparation of the compound of Formula IV. $R^3$ is lower alkyl and is the same in the malonate ester and in the alcohol. So, for example, the solvent comprises ethanol if the ester is diethyl malonate, and the solvent comprises methanol if the ester is dimethyl malonate. As used herein "lower alkyl" means a straight or branched alkyl group having from 1 to 5 carbon atoms.

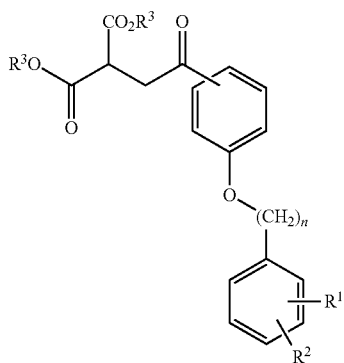

Preferably the malonate ester is diethyl malonate, the alcohol is ethanol, and the base used is sodium ethoxide or potassium ethoxide. Preferably, the solvent comprises ethanol and a polar co-solvent. Examples of acceptable polar co-solvents include THF, dioxane, DMF, DMSO, and NMP. Most preferably reaction step (b) is performed in THF/ethanol as solvent. If the malonate ester is dimethyl malonate and the alcohol is methanol, then preferably sodium methoxide or potassium methoxide is used as the base.

(c) hydrolyzing the compound of Formula IV from step (b) to yield the compound of Formula V.

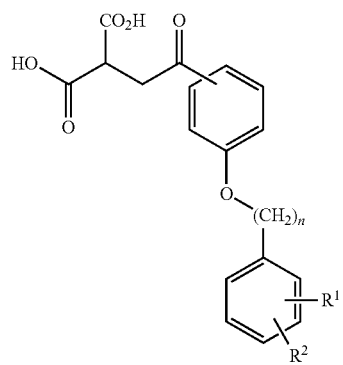

In an embodiment of this invention the hydrolysis of step (c) is performed by treating the compound of Formula IV with sodium hydroxide in water/ethanol and at a temperature between ambient and reflux, for example from 30° C. to 80° C., more specifically about 50° C.

(c') Optionally, extracting the compound of Formula V from the solution produced in step (c);

(d) decarboxylating the compound of Formula V from the previous step (c or c') to yield the compound of Formula I. In an embodiment of this invention, the decarboxylation of step (d) is performed by heating the compound of Formula V in toluene at reflux;

(d') Optionally, crystallizing or extracting the compound of Formula I from step (d) to yield isolated 4-[3-(2,6-dimethylbenzyloxy)phenyl]-4-oxobutanoic acid.

When $R^1$ and/or $R^2$ are hydroxyl groups, their protection may be beneficial to the execution of these synthetic operations. A wide variety of ether functionality can be used to protect these groups. Methods for protection and subsequent de-protection of the hydroxyl group are well known in the literature such as Greene's Protective Groups in Organic Synthesis, Fourth Edition by P. G. M. Wuts and T. W. Greene, Wiley-Interscience, Hoboken, N.J., 2007.

In an embodiment of this invention, $R^1$ is methyl at the 2-position, and $R^2$ is methyl at the 6-position. In an embodiment of this invention, wherein n is 1. In an embodiment of this invention, in Formula I the oxoacid group and the phenylalkyloxy group are in the meta orientation with respect to one another around the central phenyl ring depicted. In a specific embodiment of this invention, the compound of Formula I is 4-[3-(2,6-dimethylbenzyloxy)phenyl]-4-oxobutanoic acid.

In one embodiment this invention provides a method for producing 4-[3-(2,6-dimethylbenzyloxy)phenyl]-4-oxobutanoic acid, comprising the following steps:

(a) React 3-(2,6-dimethylbenzyloxy)acetophenone with a halogenating agent in an ethereal solvent to yield crude 2-halo-1-(3-(2,6-dimethylbenzyloxy)phenyl)ethanone. As used herein "halo" has its usual meaning and is selected from the group consisting of fluoro, chloro, bromo and iodo. In a more specific embodiment of this method the halogenating agent is a brominating agent, for example bromine, and the 2-halo-1-(3-(2,6-dimethylbenzyloxy)phenyl)ethanone is 2-bromo-1-(3-(2,6-dimethylbenzyloxy)phenyl)ethanone; or the halogenating agent is a chlorinating agent, for example sulfuryl chloride, and the 2-halo-1-(3-(2,6-dimethylbenzyloxy)phenyl)ethanone is 2-chloro-1-(3-(2,6-dimethylbenzyloxy)phenyl)ethanone. The reaction of step (a) can be performed at any temperature that is conventional for halogenations reactions. A temperature of from −30° C. to +20° C., for example a temperature of about 0° C. is convenient.

In accordance with this invention any ethereal solvent or mixture of ethereal solvents can be utilized in step (a). Examples of acceptable ethereal solvents include diethyl ether, dioxane, tetrahydrofuran (THF), and di-n-butyl ether. The preferred solvent is a mixture of dioxane and di-n-butyl ether since it gave cleaner reactions and higher yields. The yield of reaction step (a) is affected by the choice of solvent because 3-(2,6-dimethylbenzyloxy)acetophenone (DPE) is naturally prone to halogenate at other sites and/or decompose. Brominating DPE in certain other solvents such as di-n-butyl ether/THF, dichloromethane, methanol, or acetic acid gave increased amounts of by-products that are probably due to debenzylation of the starting material, or brominated product, by the HBr generated in the reaction. Some of the desired compound was also observed when DPE was treated with bromine and aluminum chloride in di-n-butyl ether, or with cupric bromide in ethyl acetate/chloroform. These reactions, however, were not as clean as the reaction in dioxane/di-n-butyl ether. Treatment of DPE with NBS or NCS in dichloromethane failed to give any halogenated product. Reaction of DPE with sulfuryl chloride gave some of the desired alpha-chloro compound, but a number of by-products were also produced. When DPE was reacted with 1,3-dibromo-5,5-dimethylhydantoin, a brominated aromatic substitution product was produced. In this case, the methyl ketone was not brominated.

(a') Optionally, triturate the crude 2-halo-1-(3-(2,6-dimethylbenzyloxy)phenyl)ethanone from step (a) to yield solid 2-halo-1-(3-(2,6-dimethylbenzyloxy)phenyl)ethanone. In a more specific embodiment the trituration is performed in methanol as solvent;

(b) React the 2-halo-1-(3-(2,6-dimethylbenzyloxy)phenyl)ethanone from the previous step with diethyl malonate and a base in a solvent, wherein the solvent comprises ethanol, to yield crude diethyl 2-(2-(3-(2,6-dimethylbenzyloxy)phenyl)-2-oxoethyl)malonate. Preferably the base used is sodium ethoxide. Preferably, the solvent comprises ethanol and a polar co-solvent. Examples of acceptable polar co-solvents include THF, dioxane, DMF, DMSO, and NMP. Most preferably reaction step (b) is performed in THF/ethanol as solvent. The sodium ethoxide base and ethanol solvent are useful in that they give high yields. The use of ethanol as solvent avoids the trans-esterification that would occur in other alcoholic solvents such as methanol. The co-solvent improves the solubility of the substrate and thereby improves the yield.

(c) Hydrolyze the diethyl 2-(2-(3-(2,6-dimethylbenzyloxy)phenyl)-2-oxoethyl) malonate from step (b) to yield 2-(2-(3-(2,6-dimethylbenzyloxy)phenyl)-2-oxoethyl) malonic acid. In an embodiment of this invention, the hydrolysis of step (c) is performed by treating the diethyl 2-(2-(3-(2,6-dimethylbenzyloxy)phenyl)-2-oxoethyl)malonate with sodium hydroxide in water/ethanol and at a temperature between ambient and reflux. In more specific embodiments, the temperature between ambient and reflux is from +30° C. to +80° C., for example about +50° C.;

(c') Optionally, extracting the 2-(2-(3-(2,6-dimethylbenzyloxy)phenyl)-2-oxoethyl)malonic acid from the solution produced in step (c);

(d) Decarboxylate the 2-(2-(3-(2,6-dimethylbenzyloxy)phenyl)-2-oxoethyl)malonic acid from the previous step to yield 4-[3-(2,6-dimethylbenzyloxy)phenyl]-4-oxobutanoic acid. In an embodiment of this invention, the decarboxylation of step (d) is performed by heating the 2-(2-(3-(2,6-dimethylbenzyloxy)phenyl)-2-oxoethyl)malonic acid in toluene at reflux;

(d') Optionally, crystallizing or extracting the 4-[3-(2,6-dimethylbenzyloxy)phenyl]-4-oxobutanoic acid from step (d) to yield isolated 4-[3-(2,6-dimethylbenzyloxy)phenyl]-4-oxobutanoic acid.

In preferred embodiments, this invention provides a method for producing 4-[3-(2,6-dimethylbenzyloxy)phenyl]-4-oxobutanoic acid, comprising: (a) reacting 3-(2,6-dimethylbenzyloxy)acetophenone with bromine in dioxane/di-n-butyl ether at about 0° C. to yield 2-bromo-1-(3-(2,6-dimethylbenzyloxy)phenyl)ethanone; (a') optionally, triturating the crude 2-bromo-1-(3-(2,6-dimethylbenzyloxy)phenyl)ethanone from step (a) in methanol to yield solid 2-bromo-1-(3-(2,6-dimethylbenzyloxy)phenyl)ethanone; (b) reacting the 2-bromo-1-(3-(2,6-dimethylbenzyloxy)phenyl)ethanone from the previous step with diethyl malonate and a base in THF/ethanol to yield a crude preparation of diethyl 2-(2-(3-(2,6-dimethylbenzyloxy)phenyl)-2-oxoethyl)malonate; (c) treating the diethyl 2-(2-(3-(2,6-dimethylbenzyloxy)phenyl)-2-oxoethyl)malonate from step (b) with sodium hydroxide in water/ethanol at about +50° C. to yield a solution comprising 2-(2-(3-(2,6-dimethylbenzyloxy)phenyl)-2-oxoethyl)malonic acid; (d) extracting the 2-(2-(3-(2,6-dimethylbenzyloxy)phenyl)-2-oxoethyl)malonic acid from the solution produced in step (c); (e) heating the 2-(2-(3-(2,6-dimethylbenzyloxy)phenyl)-2-oxoethyl)malonic acid from step (d) in toluene at reflux to yield a solution comprising 4-[3-(2,6-dimethylbenzyloxy)phenyl]-4-oxobutanoic acid; and (f) extracting the 4-[3-(2,6-dimethylbenzyloxy)phenyl]-4-oxobutanoic acid from the solution to yield isolated 4-[3-(2,6-dimethylbenzyloxy)phenyl]-4-oxobutanoic acid. Preferably the base utilized in step (b) is sodium ethoxide.

Each of the reaction steps constitutes a separate invention. Accordingly, for example, this invention provides a method for producing 2-halo-1-(3-(2,6-dimethylbenzyloxy)phenyl)ethanone, comprising reacting 3-(2,6-dimethylbenzyloxy)acetophenone with a halogenating agent in an ethereal solvent to yield crude 2-halo-1-(3-(2,6-dimethylbenzyloxy)phenyl)ethanone. In a more specific embodiment of this method the halogenating agent is a brominating agent, for example bromine, and the 2-halo-1-(3-(2,6-dimethylbenzyloxy)phenyl)ethanone is 2-bromo-1-(3-(2,6-dimethylbenzyloxy)phenyl)ethanone; or the halogenating agent is a chlorinating agent, for example sulfuryl chloride, and the 2-halo-1-(3-(2,6-dimethylbenzyloxy)phenyl)ethanone is 2-chloro-1-(3-(2,6-dimethylbenzyloxy)phenyl)ethanone. The reaction can be performed at any temperature that is conventional for halogenations reactions. A temperature of from −30° C. to +20° C., for example a temperature of about 0° C. is convenient. In accordance with this invention any ethereal solvent or mixture of ethereal solvents can be utilized. Examples of acceptable ethereal solvents include diethyl ether, dioxane, tetrahydrofuran (THF), and di-n-butyl ether. The preferred solvent is a mixture of dioxane and di-n-butyl ether. Preferably this reaction is performed in dioxane/di-n-butyl ether as solvent and at a temperature of from −30° C. to +20° C., for example at a temperature of about 0° C. Optionally, the method further comprises triturating the crude 2-halo-1-(3-(2,6-dimethylbenzyloxy)phenyl)ethanone to yield solid 2-halo-1-(3-(2,6-dimethylbenzyloxy)phenyl)ethanone. In a more specific embodiment the trituration is performed in methanol as solvent.

This invention provides a method for producing diethyl 2-(2-(3-(2,6-dimethylbenzyloxy)phenyl)-2-oxoethyl)malonate, comprising reacting 2-halo-1-(3-(2,6-dimethylbenzyloxy)phenyl)ethanone with diethyl malonate and a base in a solvent, wherein the solvent comprises ethanol, to yield a crude preparation of diethyl 2-(2-(3-(2,6-dimethylbenzyloxy)phenyl)-2-oxoethyl)malonate. "Halo" is as defined above. Preferably the "halo" compound is 2-bromo-1-(3-(2,6-dimethylbenzyloxy)phenyl)ethanone. Preferably the base is sodium ethoxide. Preferably, the solvent comprises ethanol and a polar co-solvent. Examples of acceptable polar co-solvents include THF, dioxane, DMF, DMSO, and NMP. Most preferably reaction step (b) is performed in THF/ethanol as solvent.

This invention provides a method for producing 2-(2-(3-(2,6-dimethylbenzyloxy)phenyl)-2-oxoethyl)malonic acid, comprising hydrolyzing diethyl 2-(2-(3-(2,6-dimethylbenzyloxy)phenyl)-2-oxoethyl)malonate to yield a solution comprising 2-(2-(3-(2,6-dimethylbenzyloxy)phenyl)-2-oxoethyl)malonic acid. In an embodiment of this invention, the hydrolysis is performed by treating the diethyl 2-(2-(3-(2,6-dimethylbenzyloxy)phenyl)-2-oxoethyl)malonate with sodium hydroxide in water/ethanol and at a temperature between ambient and reflux. In more specific embodiments, the temperature between ambient and reflux is from +30° C. to +80° C., for example about +50° C. In a further embodiment, the 2-(2-(3-(2,6-dimethylbenzyloxy)phenyl)-2-oxoethyl)malonic acid is extracted from the solution.

This invention provides a method for producing 4-[3-(2,6-dimethylbenzyloxy)phenyl]-4-oxobutanoic acid, comprising: (a) decarboxylating 2-(2-(3-(2,6-dimethylbenzyloxy)phenyl)-2-oxoethyl)malonic acid to yield a solution comprising 4-[3-(2,6-dimethylbenzyloxy)phenyl]-4-oxobutanoic acid; and (b) crystallizing or extracting the 4-[3-(2,6-dimethylbenzyloxy)phenyl]-4-oxobutanoic acid from the solution to yield isolated 4-[3-(2,6-dimethylbenzyloxy)phenyl]-4-oxobutanoic acid. In a more specific embodiment of this invention, the decarboxylation of step (a) is performed by heating the 2-(2-(3-(2,6-dimethylbenzyloxy)phenyl)-2-oxoethyl)malonic acid in toluene at reflux.

The invention will be better understood by reference to the following examples, which illustrate but do not limit the invention described herein.

EXAMPLES

Experimental Procedures 2-bromo-1-(3-(2,6-dimethylbenzyloxy)phenyl)etha-none

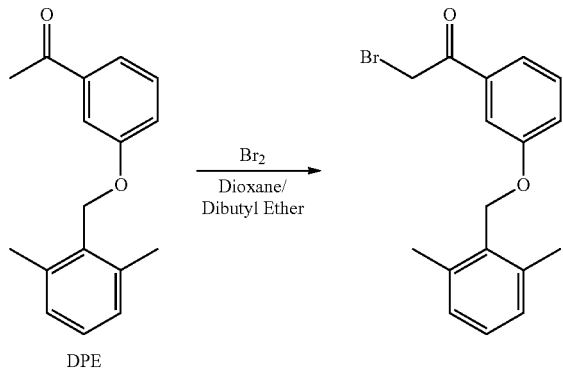 [SMILES: CC(=O)c1cccc(OCc2c(C)cccc2C)c1 ; "Br2" ; Cc1cccc(C)c1COc1cccc(C(=O)CBr)c1]

DPE

A solution of 3-(2,6-dimethylbenzyloxy)acetophenone (5.0 g, 19.7 mmol) in dioxane (30 ml) and di-n-butyl ether (15 ml) was cooled to 0° C. Bromine (3.4 g, 21.3 mmol) was added to the mixture in portions over 10 minutes. The red color due to bromine decolorized rapidly, and the mixture was stirred for a total of 15 minutes at 0° C. The reaction mixture was extracted with ethyl acetate (50 ml) and water (50 ml). The organic layer was extracted again with water (50 ml) and then with brine (50 ml). Sodium sulfate was added to dry the organic extract, and the mixture was filtered. Evaporation of the solvent under vacuum gave a residue that was triturated with methanol to give a solid suspension. The mixture was cooled to 5° C., and the solid was collected by filtration. The collected solid was washed with cold methanol (3 ml) and dried under vacuum to give 5.9 grams (90% yield) of 2-bromo-1-(3-(2,6-dimethylbenzyloxy)phenyl)ethanone. NMR (CDCl$_3$, δ) 7.62 (q, 1H), 7.58 (dt, 1H), 7.42 (t, 1H), 7.16-7.26 (m, 2H), 7.08-7.10 (2s, 2H), 5.09 (s, 2H), 4.45 (s, 2H), 2.4 (s, 6H). HPLC: Bromoketone-11.58 minutes.

4-[3-(2,6-dimethylbenzyloxy)-phenyl]-4-oxobutanoic acid

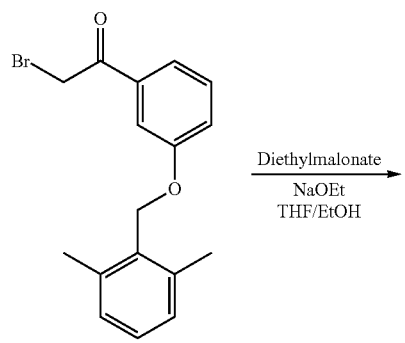

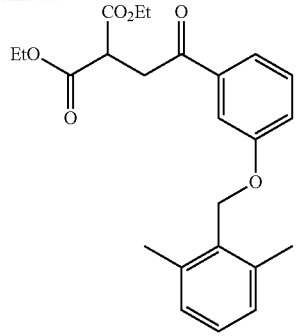

To a solution of 2-bromo-1-(3-(2,6-dimethylbenzyloxy)phenyl)ethanone (4.0 g, 12 mmol) in THF (20 ml) at 25° C. was added over 5 minutes a solution of diethyl malonate (2.0 g, 25 mmol) and sodium ethoxide (0.95 g, 14 mmol) in ethanol (20 ml). After the mixture was stirred at 25° C. for 2 hours, the solvent was evaporated under vacuum. The residue was extracted with ethyl acetate (100 ml) and aqueous 1M citric acid (100 ml). The organic layer was washed with water and then brine and dried over sodium sulfate. The extract was filtered, and the solvent was evaporated under vacuum to give 6.8 grams of the crude product, diethyl 2-(2-(3-(2,6-dimethylbenzyloxy)phenyl)-2-oxoethyl)malonate, as an oil. NMR (CDCl$_3$, δ) 7.6-7.7 (m, 2H), 7.41 (t, 1H), 7.16-7.24 (m, 2H), 7.07-7.12 (2s, 2H), 5.08 (s, 2H), 4.23 (q, 4H), 4.06 (t, 1H), 3.63 (d, 2H), 2.39 (s, 6H). HPLC: Keto diester-12.49 minutes.

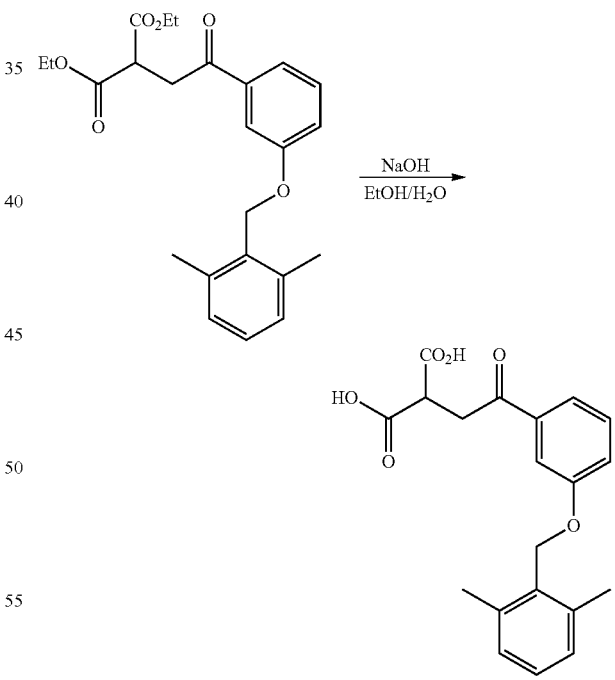

The crude diester (6.8 g) was dissolved in ethanol (70 ml), and a solution of sodium hydroxide (4.0 g, 100 mmol) in water (35 ml) was added. The suspension was heated to 50° C. for 2 hours and allowed to cool to room temperature overnight. Evaporation of the ethanol under vacuum gave a residue that was extracted with MTBE (50 ml) and water (150 ml). The MTBE layer was washed with water, 50 ml, and the combined water extract was acidified with hydrochloric acid to pH 2. The water suspension was extracted with ethyl acetate (70 ml). The organic layer was washed with water (40 ml) and brine (40 ml). The ethyl acetate extract was dried over sodium sulfate and filtered. The solvent was evaporated under vacuum to give 4.8 grams of 2-(2-(3-(2,6-dimethylbenzyloxy)phenyl)-2-oxoethyl)malonic acid as an oil. NMR (d$_6$ acetone, δ) 11.5 (bs, 2H), 7.69-7.71 (m, 2H), 7.49 (t, 1H), 7.29-7.32 (dq, 1H), 7.14-7.18 (dd, 1H), 7.08-7.1 (2s, 2H), 5.23 (s, 2H), 4.03 (t, 1H), 3.68 (d, 2H), 2.39 (s, 6H), 1.29 (t, 6H). HPLC: Diacid-8.04 minutes.

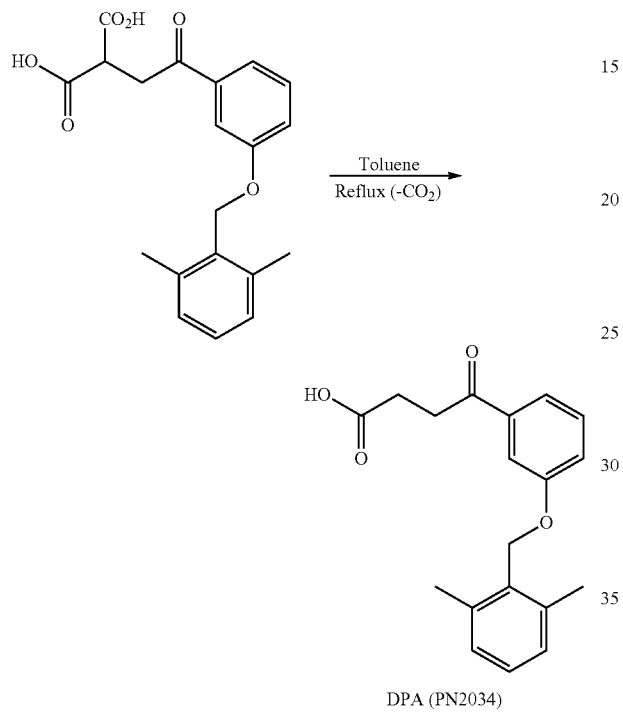

DPA (PN2034)

The 2-(2-(3-(2,6-dimethylbenzyloxy)phenyl)-2-oxoethyl) malonic acid (4.8 g) was suspended in toluene (20 ml), and the mixture was heated to reflux for 7 hours. The mixture was allowed to cool to room temperature overnight. The desired product crystallized out, and the suspension was stored at 5° C. for 4 hours. The solid was collected by filtration and dried under vacuum to give 2.2 grams of 4-[3-(2,6-dimethylbenzyloxy)-phenyl]-4-oxobutanoic acid. The mother liquor was evaporated and the residue was triturated with saturated sodium bicarbonate solution (2×50 ml). The aqueous solution was filtered, and the filtrate was acidified with hydrochloric acid to pH 1. The resulting suspension was extracted with ethyl acetate (100 ml), and the organic layer was washed with brine. The ethyl acetate extract was dried over sodium sulfate, filtered, and evaporated under vacuum to give an additional 0.4 grams of the desired product. Total of 2.6 g (69% yield). NMR (CDCl$_3$, δ) 7.59-7.65 (m, 2H), 7.40 (t, 1H), 7.15-7.23 (m 2H), 7.06-7.10 (2s, 2H), 5.09 (s, 2H), 3.32 (t, 2H), 2.82 (t, 2H), 2.39 (s, 6H). HPLC: DPA-9.02 minutes.

HPLC Conditions Summary

Agilent Zorbax SDC8, 4.6×100 mm, 3.5 micron, 35° C.

Agilent 1100 HPLC, UV detection at 254 nm, 1.25 mL/min throughout

C=0.1% TFA in acetonitrile; D=0.1% TFA in water

| Time (min) | % C | % D |
|---|---|---|
| 0 | 20 | 80 |
| 15 | 90 | 10 |
| 16 | 20 | 80 |

What is claimed is:

1. A method for producing a compound of Formula I

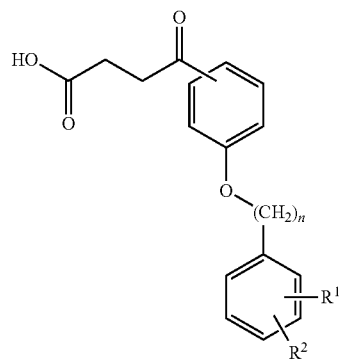

wherein n is 1, 2 or 3;

R$^1$ and R$^2$ are each independently selected from the group consisting of halo, alkyl having one or two carbon atoms, perfluoromethyl, alkoxy having one or two carbon atoms, perfluoromethoxy, and hydroxy;

comprising:

(a) reacting the corresponding compound of Formula II with a halogenating agent in an ethereal solvent to yield crude compound of Formula III, wherein X is fluoro, chloro, bromo or iodo;

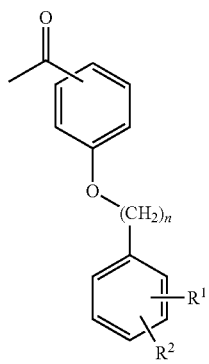

-continued

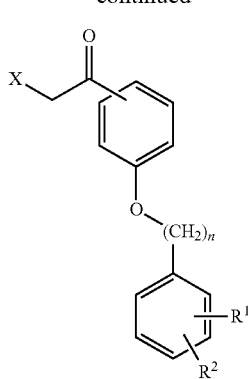

III (b) reacting the compound of Formula III from the previous step with a malonate ester represented by the formula $R^3OC(O)CH_2C(O)OR^3$ and a base in a solvent, wherein the solvent comprises an alcohol represented by the formula $R^3OH$, wherein $R^3$ is lower alkyl, to yield a crude preparation of the compound of Formula IV;

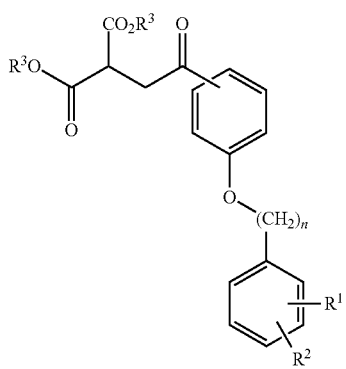

IV (c) hydrolyzing the compound of Formula IV from step (b) to yield the compound of Formula V; and

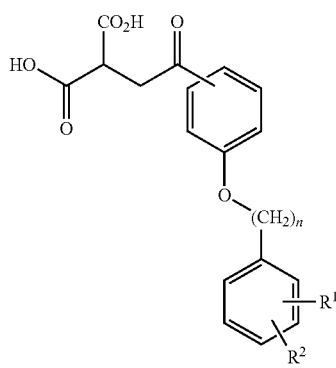

V (d) decarboxylating the compound of Formula V from the previous step to yield the compound of Formula I.

2. The method of claim 1, wherein the compound of Formula I is 4-[3-(2,6-dimethylbenzyloxy)phenyl]-4-oxobutanoic acid.

3. A method for producing 4-[3-(2,6-dimethylbenzyloxy)phenyl]-4-oxobutanoic acid, comprising:

(a) reacting 3-(2,6-dimethylbenzyloxy)acetophenone with bromine in dioxane/di-n-butyl ether at about 0° C. to yield 2-bromo-1-(3-(2,6-dimethylbenzyloxy)phenyl)ethanone;

(b) reacting the 2-bromo-1-(3-(2,6-dimethylbenzyloxy)phenyl)ethanone from the previous step with diethyl malonate and a base in THF/ethanol to yield a crude preparation of diethyl 2-(2-(3-(2,6-dimethylbenzyloxy)phenyl)-2-oxoethyl)malonate;

(c) treating the diethyl 2-(2-(3-(2,6-dimethylbenzyloxy)phenyl)-2-oxoethyl)malonate from step (b) with sodium hydroxide in water/ethanol at about +50° C. to yield a solution comprising 2-(2-(3-(2,6-dimethylbenzyloxy)phenyl)-2-oxoethyl)malonic acid;

(d) extracting the 2-(2-(3-(2,6-dimethylbenzyloxy)phenyl)-2-oxoethyl)malonic acid from the solution produced in step (c);

(e) heating the 2-(2-(3-(2,6-dimethylbenzyloxy)phenyl)-2-oxoethyl)malonic acid from step (d) in toluene at reflux to yield a solution comprising 4-[3-(2,6-dimethylbenzyloxy)phenyl]-4-oxobutanoic acid;

(f) extracting the 4-[3-(2,6-dimethylbenzyloxy)phenyl]-4-oxobutanoic acid from the solution to yield isolated 4-[3-(2,6-dimethylbenzyloxy)phenyl]-4-oxobutanoic acid.

4. The method of claim 3, further comprising triturating the crude 2-bromo-1-(3-(2,6-dimethylbenzyloxy)phenyl)ethanone from step (a) in methanol to yield solid 2-bromo-1-(3-(2,6-dimethylbenzyloxy)phenyl)ethanone.

5. The method of claim 3, where in step (b) the base is sodium ethoxide.

6. A method for producing diethyl 2-(2-(3-(2,6-dimethylbenzyloxy)phenyl)-2-oxoethyl)malonate, comprising reacting 2-bromo-1-(3-(2,6-dimethylbenzyloxy)phenyl)ethanone with diethyl malonate and a base in a solvent, wherein the solvent comprises ethanol, to yield a crude preparation of diethyl 2-(2-(3-(2,6-dimethylbenzyloxy)phenyl)-2-oxoethyl)malonate.

7. The method of claim 6, wherein the base is sodium ethoxide.

8. The method of claim 6, wherein the reaction is performed in THF/ethanol as solvent.

9. A method for producing 2-(2-(3-(2,6-dimethylbenzyloxy)phenyl)-2-oxoethyl)malonic acid, comprising hydrolyzing diethyl 2-(2-(3-(2,6-dimethylbenzyloxy)phenyl)-2-oxoethyl)malonate to yield a solution comprising 2-(2-(3-(2,6-dimethylbenzyloxy)phenyl)-2-oxoethyl)malonic acid.

10. The method of claim 9, wherein the hydrolysis is performed by treating the diethyl 2-(2-(3-(2,6-dimethylbenzyloxy)phenyl)-2-oxoethyl)malonate with sodium hydroxide in water/ethanol and at a temperature of from +30° C. to +80° C.

11. The method of claim 10, wherein the hydrolysis is performed at a temperature of about +50° C.

12. The method of claim 9, further comprising extracting the 2-(2-(3-(2,6-dimethylbenzyloxy)phenyl)-2-oxoethyl)malonic acid from the solution.

13. A method for producing 4-[3-(2,6-dimethylbenzyloxy)phenyl]-4-oxobutanoic acid, comprising:

(a) decarboxylating 2-(2-(3-(2,6-dimethylbenzyloxy)phenyl)-2-oxoethyl)malonic acid to yield a solution comprising 4-[3-(2,6-dimethylbenzyloxy)phenyl]-4-oxobutanoic acid; and (b) crystallizing or extracting the 4-[3-(2,6-dimethylbenzyloxy)phenyl]-4-oxobutanoic acid from the solution to yield isolated 4-[3-(2,6-dimethylbenzyloxy)phenyl]-4-oxobutanoic acid.

14. The method of claim 13, wherein the decarboxylation of step (a) is performed by heating the 2-(2-(3-(2,6-dimethylbenzyloxy)phenyl)-2-oxoethyl)malonic acid in toluene at reflux.

* * * * *

UNITED STATES PATENT AND TRADEMARK OFFICE
CERTIFICATE OF CORRECTION

PATENT NO. : 8,703,991 B2
APPLICATION NO. : 13/127120
DATED : April 22, 2014
INVENTOR(S) : Wirth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 283 days.

Signed and Sealed this
Twenty-ninth Day of September, 2015

Michelle K. Lee
*Director of the United States Patent and Trademark Office*